United States Patent [19]

Gaffar et al.

[11] Patent Number: 5,096,699
[45] Date of Patent: Mar. 17, 1992

[54] ANTICALCULUS ORAL COMPOSITIONS

[75] Inventors: Abdul Gaffar, Princeton; John J. Afflitto, Brookside; Marilou T. Joziak, South River, all of N.J.

[73] Assignee: Colgate-Palmolive Company, Piscataway, N.J.

[21] Appl. No.: 631,232

[22] Filed: Dec. 20, 1990

[51] Int. Cl.$^5$ .............................. A61K 7/16; A61K 7/22
[52] U.S. Cl. .......................................... 424/49; 424/54
[58] Field of Search ..................................... 424/49-58

[56] References Cited

U.S. PATENT DOCUMENTS

| | | | |
|---|---|---|---|
| 3,925,456 | 12/1975 | Ploger et al. | 424/54 |
| 3,941,772 | 3/1976 | Ploger et al. | 424/54 |
| 3,984,543 | 10/1976 | Ploger et al. | 424/49 |
| 3,988,443 | 10/1976 | Ploger et al. | 514/891 |
| 4,108,961 | 8/1978 | Ploger et al. | 424/57 |
| 4,108,962 | 8/1978 | Ploger et al. | 424/57 |

*Primary Examiner*—Shep K. Rose
*Attorney, Agent, or Firm*—Robert L. Stone; Murray M. Grill

[57] ABSTRACT

An anticalculus oral composition, which is preferably a toothpaste or a mouthrinse, includes an effective anticalculus azacycloalkane-2,2-diphosphonic acid or a salt thereof, preferably azacycloheptane-2,2-diphosphonic acid, and a polymeric polycarboxylate, which is preferably a linear copolymer of maleic anhydride and vinyl methyl ether of a molecular weight in the range of about 5,000-2,000,000, preferably about 30,000-1,500,000. The copolymer surprisingly increases the anticalculus effectiveness of the azacycloalkane-2,2-diphosphonic acid or salt thereof in such compositions, even at comparatively low concentrations of both such materials.

Also within the invention is a process for applying such compositions to the teeth, and it has been shown by both in vitro and in vivo testing that significant and repeatable improvements in anticalculus effects are obtained by such processes, compared to control processes in which either of the active components mentioned is employed alone in the described anticalculus oral compositions.

21 Claims, No Drawings

ANTICALCULUS ORAL COMPOSITIONS

This invention relates to anticalculus oral compositions. More particularly, it relates to such compositions which are intended for application to the teeth and which have the desirable property of effectively inhibiting development of dental calculus, which development can lead to gingivitis.

Toothpastes and mouthrinses have been manufactured and sold which have had in their formulas components intended to promote dental health, in addition to components intended primarily to clean the teeth and sweeten the breath. For examples, fluorides have been successfully included in dentifrice formulations and in mouthrinse for years to harden teeth and reduce caries development, and triclosan and sanguinaria (bloodroot) extract have been employed in dentifrices to reduce plaque formation on the teeth. Azacycloalkane-2,2-diphosphonic acids (AAP's), especially azacycloheptane-2,2-diphosphonic acid (AHP), and salts thereof (also designated AAP and AHP) have been suggested for incorporation in dentifrices to reduce tartar and plaque because they have the ability to dissolve or prevent deposition on the teeth of difficultly soluble calcium salts. Also, synthetic anionic polymeric polycarboxylates (SAPP's), such as copolymers of maleic anhydride or maleic acid with vinyl methyl ether, have been suggested for incorporation in dentifrices together with fluorides and pyrophosphates. Thus, the art was aware of AAP and SAPP being used as dentifrice components but does not disclose them as having been used together or that if so used that they would have any special or unexpected effects. Therefore, the combination of both such compounds in dentifrices or oral preparations is novel and is unobvious, especially in view of the unexpectedly beneficial increased anticalculus action resulting.

In accordance with the present invention an anticalculus oral composition comprises an orally acceptable vehicle or base for such composition, an effective anticalculus proportion of an orally acceptable azacycloalkane-2,2-diphosphonic compound (AAP) selected from the group consisting of compounds of the formula

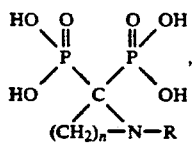

wherein R is selected from the group consisting of hydrogen and alkyls of 1 to 3 carbon atoms and n is an integer from 3 to 5, and orally acceptable salts thereof, and a synthetic anionic polymeric polycarboxylate (SAPP) of a molecular weight in the range of about 5,000-2,000,000, in a proportion which is effective to increase the anticalculus action of the AAP in the described composition.

Applicants are aware of and call attention to the following patent art of interest:

U.S. Pat. Nos. 3,941,772 and 3,988,443, which relate to azacycloalkane-2,2-diphosphonic acids and their uses in toothpastes and mouthwashes to delay formation of tartar and plaque;

U.S. Pat. Nos. 4,323,551, 4,515,772, 4,627,977 and 4,931,27 which disclose a copolymer of maleic anhydride or maleic acid with vinyl methyl ether (Gantrez®) in dentifrices, as do published European Pat. applications Nos. 89114192.1 and 89200710.5 and U.S Pat. applications Ser. Nos. 07/505,628, 07/547,641 and 07/547,642, with the last three U.S. applications also disclosing triclosan in such dentifrices as an antibacterial agent which inhibits deposition of plaque on the teeth; and U.S. Pat. No. 4,002,880, which discloses triclosan as an antibacterial agent in dentifrices together with a source of zinc ions, which acts as an anticalculus agent, and German OLS 3532860, in which triclosan is disclosed in a dentifrice with a copper compound.

From a review of such art it appears that AAP, AHP, SAPP and triclosan are all known dentifrice components, separately and in some two-member combinations, but no references are known to applicants in which AAP, SAPP and triclosan are present together or in which any AAP and SAPP are present together, in a dentifrice or other oral preparation, or in which such preparations are suggested. Thus, the claimed compositions and processes are novel and unobvious. The unexpectedly beneficial improvement in the anticalculus action of the AAP that results from incorporation of the SAPP in oral compositions with the AAP is very surprising in view of the negligible anticalculus activity of the SAPP alone in such compositions. The improvement is significant, often being more than 30% by both in vitro testing, in which precipitation of hydroxyapatite from a supersaturated solution onto hard substrates wa delayed by that much time, and by in vivo testing, in which calculus formation, as actually measured, was found to have been decreased.

The AAP or azacycloalkane-2,2-diphosphonic compound of the invented compositions is an orally acceptable phosphonic acid or said thereof, and if the salt is employed it will usually be the sodium or potassium salt and will be water soluble. If a salt is to be used it will preferably be one wherein more than one of the phosphon hydroxyl hydrogens is replaced by the desired alkali metal, such as sodium. The acid form of the AAP is of the following formula:

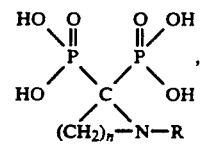

wherein R is selected from the group consisting of hydrogen and alkyls of 1 to 3 carbon atoms and n is an integer from 3 to 5. Preferably R will be hydrogen and n will be 5, forming an azacycloheptyl group. Although the salts of the described diphosphonic acids may be employed in the present compositions and although the acid form may be converted or partially converted to salt form in situ in some oral preparations, it will generally be preferred to utilize the acid form of the AAP in the present compositions.

It will be noted that it has been said herein that the AAP utilized should be "orally acceptable". In the present context and throughout this specification that means that the material so specified should be non-toxic, harmless to the mouth, gums and teeth and of acceptable flavor (or none at all). It should also be essentially compatible with the other components of the oral preparation in which it is to be formulated. It has been determined that the described AAP's satisfactorily pass such tests.

The synthetic anionic polymeric polycarboxylate (SAPP), which is the other main component of the present oral compositions improves the anticalculus action of the AAP and may also function to inhibit the action of alkaline phosphatase enzyme, which otherwise could have a negative effect on polyphosphate, such as pyrophosphates which can be present as an anticalculus agent in the present compositions, in addition to the AAP. Such SAPP's and their complexes with cationic germicides and metals, such as zinc and magnesium, have been described in U.S. Pat. Nos. 3,429,963, 3,956,480, 4,138,477, 4,152,420, 4,183,914 and 4,627,977.

The described SAPP's are preferably employed as partially or completely neutralized water soluble or water swellable alkali metal (or ammonium) salts but may also be used as their free acids. Preferably they are 4:1 to 1:4 copolymers of maleic anhydride or maleic acid with another polymerizable ethylenically unsaturated monomer, which is very preferably methyl vinyl ether, and the co-polymer will have a molecular weight in the range of about 5,000–2,000,000, preferably about 30,000–1,500,000, more preferablly about 50,000–1,100,000 and most preferably about 50,000–100,000, as determined by vapor pressure osmometry. A preferred range of molecule weights, by gel permeation chromatography against a polyethylene glycol standard is about 500,000–1,500,000, more preferably about 1,000,000–1,100,000, e.g., about 1,090,000. Useful such SAPP's include GAF's Gantrezes AN 169, AN 139, AN 119 and S-97, pharmaceutical grade. These SAPP's have been reported by their manufacturer to be molecular weights of about 750,000, 500,000, 250,000 and 70,000, respectively, but by gel permeation chromatography determinations (against a polyethylene glycol standard) the S-97, pharmaceutical grade, is of a molecular weight in the range of about 1,000,000–1,100,000 (the lower molecular weight of 70,000 was determined by vapor pressure osmometry). The mentioned Gantrezes are all linear copolymers but cross-linked polymers, such as those sold under the trademark Carbopol ®, of B.F. Goodrich, e.g., Carbopols 934, 940 and 941, may be substituted, at least in part (e.g., about 1% or more).

Instead of the mentioned polymeric polycarboxylates, other SAPP's may also be substituted in part, such as polysulfonates, polysulfates and polyphosphonates, up to about half the SAPP content. The various polymers of such types may be made by reacting an ethylenically unsaturated organic acid, such as maleic, crotonic, sorbic, alpha-chlorosorbic, cinnamic, muconic, itaconic, citraconic, mesaconic, glutaconic, aconitic, angelic, umbellic or fumaric, acid(s) or anhydride(s), with an appropriate polymerized ethylenically unsaturated carboxylic, sulfonic, sulfuric or phosphonic acid that contains an activated carbon-to-carbon olefinic double bond and at least one carboxylic, sulfonic, sulfuric or phosphonic group. Other olefinic monomers th are copolymerizable with the described acids or anhydrides include vinyl acetate, vinyl chloride, dimethyl maleate, and similar unsaturated monomers, and the copolymers made will contain a sufficient proportion of acidic groups or neutralized or neutralizable acidic groups to make them water soluble or swellable. Some such polycarboxylate copolymers are those disclosed in U.S. Pat. Nos. 4,138,477 and 4,183,914, and include copolymers of maleic anhydride with styrene, isobutylene or vinyl ethyl ether, polyacrylic, polyitaconic and polymaleic acids, and sulfoacrylic oligomers of comparatively low molecular weights, such as Uniroyal ®ND-2.

Although Gantrez is preferred, also useful in the present compositions as SAPP's or as substitutes for them in part are carboxyvinyl polymers, such as those described in U.S. Pat. Nos. 3,711,604, 3,911,904, 3,919,409, 3,935,306 and 3,980,767, wherein they were employed as components of toothpastes. Such materials are the Carbopols, mentioned previously, which are polymers of polyacrylic acid crosslinked with minor proportions of polyallyl sucrose or polyallyl pentaerythritol, as crosslinking agents. Instead of such polymers there may be employed polycarbophil, which is polyacrylic acid crosslinked with divinyl glycol.

In summary, with respect to the SAPP's, polymers that are most effective will normally be those with a sufficient proportion of carboxyls or neutralized carboxyls to be water soluble or swellable in the present oral compositions, and such will also increase the anticalculus effectiveness of AAP.

Other polymeric compounds that may also be used in oral compositions like those described herein and can increase the anticalculus activity of the AAP are described in U.S. Pat. application Ser. No. 07/398,605 in the description therein of antibacterial enhancing agents (AEA's), and such application is hereby incorporate herein by reference, as are the disclosures of the other patents, applications and publications referred to in this specification.

Antibacterial non-cationic diphenyl ethers, such as halogenated and hydroxy-substituted ethers, preferably triclosan, are included in preferred compositions of this invention for antiplaque properties (prevention of bacterial growth on the teeth). Triclosan is described in U.S. Pat. No. 4,002,880, German OLS 353286 and European Pat. applications Nos. 0161898, 0161899 and 0220890. It is of the formula 2', 4, 4'-trichloro-2-hydroxy-diphenyl ether, and is known to be an effective compound for inhibiting growth of microorganisms, especially bacteria. Another such useful compound, for example, is 2,2'-dihydroxy-5,5'-dibromo-diphenyl ether.

Another important active component of preferred embodiment of the invented compositions is a source of fluoride ions, which gives the compositions tooth hardening properties and helps to reduce caries development. The source of fluoride ions is usually inorganic and a salt, and may be fully or slightly soluble in water. Such source is characterized by an ability to release fluoride ions in water and by relative inertness toward other components of the oral compositions. Among the useful sources of fluoride ions are soluble alkali metal fluorides, such as sodium and potassium fluorides, copper fluorides, such as cuprous fluoride, tin fluorides, such as stannous fluoride, ammonium fluorosilicate, sodium fluorozirconate, ammonium fluorozirconate, sodium monofluorophosphate, aluminum fluorophosphates (mono-, di- and tri-), and fluorinated sodium calcium pyrophosphate. Alkali metal and tin fluorides, such as sodium and stannous fluorides, and sodium monofluorophosphate (MFP ®) and mixtures thereof are preferred.

Another important component of the present compositions, except sometimes for tooth powders, gums and lozenges, is water. In toothpastes and other such paste or gel compositions an aqueous base will be present and in mouthwashes and such types of liquid compositions an aqueous medium will be present, which will usually include an alcohol. The water employed may be city water and the hardness thereof may be as high as 300 or even 500 p.p.m., as calcium carbonate, in some instances, but it will be preferred to limit the hardness to no more than 100 or 150 p.p.m., and it will be more preferred to employ zero hardness water or deionized water, which is most preferably irradiated before being compounded with the other components of the oral compositions.

For the liquid state compositions of this invention, such mouthrinses or mouthwashes, professionally applied tooth hardeners, and antiplaque compositions, the liquid medium in which the active anticalculus components are dispersed and/or dissolved will normally be aqueous and often will be aqueous alcoholic, with ethanol being the preferred alcohol. A surfactant, such as a detergent, is also preferably present in most such compositions. Other adjuvants may be present too, and sometimes impurities or by-products present with the components, as commercially supplied, will also be present in the final compositions.

For the paste, gel, solid and particulate solid state compositions of the invention, such as toothpastes, gel dentifrices, tooth powders, chewing gums and lozenges, the base or medium for the active components will be such as is normally employed for such compositions that don't contain AAP and SAPP. For the toothpastes and gel dentifrices such bases will comprise: water; humectant, such as glycerol, sorbitol, mannitol, propylene glycol and/or polyethylene glycol; polishing agent, such as silica, calcium carbonate, tricalcium phosphate, dicalcium phosphate and/or insoluble sodium metaphosphate (of which finely divided silica polishing agent is preferred); and a surfactant, such as sodium lauryl sulfate, sodium N-coco, N-methyl taurate, sodium -lauroyl sarcosine or other compatible detergent. A thickener, which will preferably be a natural or synthetic gum, such as carrageenan or hydroxymethyl cellulose, or a siliceous thickener (such as fumed silica) or a mixture of such thickeners will often be employed to help to increase paste or gel viscosity or body and in the case of the gel dentifrice it can function as the gelating agent. Other known thickeners and gelating agents may be employed in place of those specifically mentioned above and other known polishing agents, humectants and surfactants may also be used. The bases for the tooth powders will normally be almost entirely of polishing agent, with some surfactant. The base for the gum can be an elastomer of type normally employed in chewing gums, e.g., chicle, gum or rubber and the lozenges may have a hard sugar or candy base but preferably will be sorbitol or of a gummy material, such as gelatin, sweetened with artificial sweetener, such as saccharin or aspartame.

The various oral compositions of this invention will often contain adjuvants to make them more acceptable to the consumer and more effective for their purposes. Because the compositions are intended for oral uses they will almost invariably include flavoring agents and sweeteners, of which mint flavors, such as peppermint and spearmint are typical, and saccharin and aspartame are favored artificial or synthetic sweeteners. Also, adjuvant materials may be present to give the compositions additional desirable properties and to increase desirable characteristics of the compositions. For example, sodium pyrophosphate may be incorporated in the compositions to decrease plaque and tartar, buffers may be added to control pH, bleaching agents and tooth whiteners may be present, and preservatives, dyes and pigments may be employed.

The proportions of the active components of the invented compositions should be within certain ranges to obtain the anticalculus effects desired. The proportion of SAPP to AAP should be such that the SAPP significantly improves the anticalculus effect of the AAP. Such significant effect may be measured in vivo, in which case the improvement obtained should be at least 10% more reduction in calculus on human or primate teeth than for a "control" from which the SAPP was omitted (but in which the AAP was present). Thus, for example, if a placebo composition, not containing either AAP or SAPP, gives 8.7 units of calculus in primates, using techniques described in *Colloids and Surfaces*, 26 (1987) 109–121, by Gaffar et al., and employing AHP in the same toothpaste lowers calculus formation to 5.7 units, then the experimental composition containing SAPP and AHP, should reduce calculus formed to 5.4 unit or less. Preferably such lowering will be at least 20% and more preferably will be at least 30%. In actuality, the calculus is reduced to 3.7 units, a reduction of 67%. Instead of employing the mentioned in vivo test an in vitro test may be substituted, in which the time of deposition of hydroxyapatite from a supersaturated calcium phosphate solution onto a substrate is measured, using a control (water solution of calcium phosphate), a comparative (water solution of calcium phosphate plus AAP), and a test solution (water solution of calcium phosphate plus AAP and SAPP). By such a test it is desirable for the test solution to delay formation of hydroxy-apatite for at least ten minutes more than the comparative solution This in vitro test is described in detail in the text *Recent Advances the Study of Dental Calculus* (IRL Press) at pages 155–173. The suitability of the in vitro test has been established by parallel testing in vivo, so either test may be employed to determine the effectivenesses of different anticalculus compositions in retarding the deposition of calculus on teeth. The mentioned article and text are both incorporated herein by reference.

Because calculus formation is related to tartar deposition on the teeth and because calculus and tartar are precursors of gum irritation and gingivitis, oral compositions that are effective in inhibiting calculus development on the teeth ca help to prevent gingivitis and thereby can help to prevent resulting tooth losses. Therefore, the present compositions are of significant importance in improving dental health, in addition to being of real importance cosmetically by keeping tooth surfaces smooth, clean and bright, and free of calculus and tartar.

The proportions of AAP and SAPP in the invented anticalculate compositions will normally be in the range of about 1:50–50:1, with about 1:30–5:1 being preferred and with about 1:10–3:1 being more preferred, e.g., 1:8, 1:5, 1:1 and 2:1. Usually one will not employ more than 3 or 5% of each of AAP and SAPP in the invented compositions and at least about 0.01% of AAP and at least about 0.1% of SAPP will be present to obtain the desired effects. In toothpastes gels and powder products the ranges of contents of AAP and SAPP will usually be about 0.2–2% of AAP and about 0.2–3% of SAPP, preferably being about 0.5–1.5% and about 0.3–1%, respectively, and more preferably being 0.8–1.2% and 0.3–0.7%, respectively. For the anticalculus mouthwashes and mouthrinses of the invention the ranges of contents of AAP and SAPP will usually be about 0.01–2% of AAP and about 0.01–3% of SAPP, preferably about 0.1–2% and 0.1–3%, respectively, more preferably about 0.3–1.5% and about 0.1 to 1%, respectively, and most preferably about 0.3–0.7% and about 0.2–0.5%, respectively.

When triclosan is present in the described compositions, for its antiplaque activity, the proportions thereof will normally be within the range of about 0.01–1%, preferably about 0.3–0.6%, and more preferably about 0.03–0.3%, with about 0.3–1% and 0.01–0.06% being present in tooth and mouth preparations, respectively. When a source of fluoride ions is present, for its tooth hardening and anticaries actions, the proportion thereof in the oral compositions will normally be in the range of about 0.01–0.5%, based on the fluoride ion content thereof, which corresponds to about 0.02–1% of sodium fluoride. Preferably the percentage of fluoride ion source (as fluoride ion) will be about 0.02–0.3%, which corresponds to about 0.04–0.6% of sodium fluoride, and more preferably such percentage range will be about 0.1–0.2% of such source, which corresponds to about 0.2–0.4% of sodium fluoride.

The proportions and percentages of other components of the oral compositions are not as directly related to the anticalculate antitartar and antiplaque activities of the oral compositions as those of the AAP, SAPP, triclosan and fluoride source, as given above but often will be those which are employed in making conventional oral compositions of the same or similar types. However, they are given here so that the reader will have guidance for making the complete anticalculus compositions.

The toothpastes and gel dentifrices of the invention will preferably contain about 15–45% of humectant and more preferably about 20–35% thereof and such humectant preferably will be selected from the group consisting of glycerol, sorbitol, mannitol, propylene glycol and polyethylene glycols. The polishing agent content will preferably be in the range of about 10–40% and more preferably will be in the range of about 10–25%, with the preferred such agent being a finely divided silica dental polishing agent. Such toothpastes and gel dentifrices will also preferably contain about 0.2–3% of a surfactant (surface active agent) and more preferably the percentage of surfactant will be in the range of about 0.5–2%, and the surfactant will preferably be an acceptable dental detergent such as sodium lauryl sulfate, other anionic detergent, such as sodium N-lauroyl sarcosine and/or sodium N-lauroyl, N-methyl taurate amphoteric detergent, such as one that is betaine based, or a nonionic detergent, such as a condensation product of a higher alcohol of 8 to 20 carbon atoms with 1 or 3 to 16 or 20 moles of ethylene oxide, or a nonionic detergent of the Pluronic ® type, e.g., Pluronic L-44. The percentage of thickener is preferably in the range of about 0.5–8%, more preferably about 1–5%, and the thickener is preferably a mixture of organic gum, such as carrageenan and finely divided silica, such as fumed silica, with the silica thickener often being present in greater proportion.

Various adjuvants present will normally total no more than about 10% of the compositions and often that total will be about 0.1–5%. Such can normally include flavor, colorant, antioxidant preservative, decorative components, such as speckles, pearlescing agents, bactericides, buffers, anti-enzymatic additives and physiologically active coolants, such as menthol. The balances of the dentifrices will be water and the proportion thereof will ordinarily be in the range of about 20–70%, preferably being in the range or about 35–55%, e.g., 45%.

The toothpastes and gel dentifrices may be packaged in conventional metal or plastic "squeeze tubes", in piston actuated dispensers, in pressurized "aerosol" dispensers or in other suitable containers, which are preferably of the dispensing type. If the container is plastic and the dentifrice contains triclosan it will be preferable to include limonene or other such stabilizing terpene in the flavor or as an adjuvant to stabilize the triclosan against any possible decomposition due to contact with such plastic under elevated temperature storage conditions. Triclosan is not decompose by all plastics but it may often be advisible to include the stabilzer in the dentifrice formulas as a safety measure.

The mouthrinses or mouthwashes of the invention do not require any additional components than the AAP, SAPP, alcohol and water, and sometimes the alcohol may be omitted. However, if alcohol is present the proportion thereof will normally be in the range of about 3–30%, preferably about 5–20%, and the balance of the composition will be water and adjuvants, in addition to the AAP an SAPP. The mouthrinses or mouthwashes may also include the other active components previously mentioned as components of the toothpastes and gel dentifrices, and usually they may be present in the same or lesser percentages, except that normally no polishing agents will be used and the proportion of humectant present, if any, will be reduced, as may be the proportion of surfactant, and water will constitute the balance of the composition, allowing for the presence of a small proportion of adjuvants, such as colorants and flavors. When the mouthrinse contains about 0.1–2% of AAP, about 0.1–2% of SAPP and about 2–30% of ethanol, for example, the water content may be in the range of about 0.6–97.8% and when it contains about 0.5–1.5% of AAP, about 0.3–1% of SAPP and about 5–20% of ethanol the water content may be in the range of about 77.5–94.2%.

For the tooth powders, the proportions of AAP, SAPP and surfactant may be the same as for the toothpastes and the balances of such compositions will normally be polishing agent plus the normal content of adjuvant(s), as for the toothpastes. Such preparations may also include a source of fluoride and triclosan, in such proportions as are employed in the toothpastes, and other tooth treating components may be present too, including pyrophosphate for tartar control.

The tooth hardening liquid compositions, which may be professionally "painted" onto the teeth, and the antiplaque liquid compositions, which may be similarly applied or may be "rinsed" onto the teeth, are similar in composition to the mouthrinses but will also contain a source of fluoride (often in the same or greater proportion as for the toothpaste and fluoride-containing mouthrinse) and triclosan (also in proportions like those for the mouthwashes and toothpastes), respectively. The gums and lozenges will also contain the same proportions of AAP and SAPP as the toothpastes, with or without fluoride source, surfactant, triclosan and adjuvants, often in the same proportions as for the toothpastes. Water content and any contents of humectant materials will be adjusted as indicated to be desirable to obtain these products in chewable gum or slowly dissolvable lozenge form.

Manufacturing of dentifrices of this invention is comparatively simple because, in general, there is little or no criticality in the order of addition of the various components present in such compositions. Initially one forms a premix of most or all of the water, in which the surfactant has been dissolved, and then triclosan is admixed with that, followed by other water soluble components and the water insoluble components, if any. If desired, the lipophilic components may be premixed together and such premix can be mixed with the hydrophiles premix, after which the water insoluble particulate materials may be blended in, as in the cases of toothpastes and gels. Such procedures are typical of those employed in manufacturing toothpastes and dentifrice gels, with the only exception being in the addition of the triclosan, if present, to the water solution of surfactant, as an initial production step.

Manufacture of the mouthrinses or mouthwashes is even simpler because in such cases the ethanol and water are mixed and the various soluble components are then admixed with such aqueous alcoholic medium, with the surfactant and triclosan, if present, preferably being admixed first with the medium. The tooth powder may be made by merely blending the various powdered components there of and the professional tooth hardening preparations and the antiplaque compositions may be made by following the procedure described for the mouthrinses. Making the gums and lozenges may be by procedures normally employed in manufacturing such products, with the active components usually preferably being added near the end of the manufacturing process if heat was employed (so as to minimize subjection to elevated temperatures).

All the processes for manufacturing the described compositions may be carried out at room temperature, as a rule, except possibly those for making gum and lozenges including AAP and SAPP, and in such cases heating may be minimized to the extent that such is practicable.

Using the invented compositions is easy, and processes for inhibiting formation of calculus on the teeth normally merely involve employing the preparations containing the AHP and SAPP in normal manners. Thus, the teeth are brushed with the toothpaste or dentifrice gel, the mouth is rinsed with the mouthrinse or mouthwash, the tooth hardener and antiplaque compositions are applied to the teeth with swabs or by rinsing the mouth with them, the gum is chewed and the lozenge is allowed to dissolve slowly in the saliva in the mouth. In all such cases use of the invented compositions (or of their separate active components) will cause a decrease in calculus development on the teeth. The teeth will be cleaner, whiter, brighter and of better appearance, and development of tartar will be reduced, thereby helping to make the teeth and gums healthier and to prevent gingivitis. If triclosan is present in the composition plaque development will also be inhibited, and if oxidizing agents are present, such as peroxides, the teeth will be still white due to bleaching of any food and other stains on them.

The improvements in the teeth, as mentioned above, are noticeable visually and diagnostically after repeated treatments with one or more of the invented compositions and for best effects the compositions should be employed on a regular daily basis, at least once a day and preferably twice, for a period of at least a month, and preferably longer. Ideally, such treatments should be ongoing, for months and even for years, just as conventional toothbrushings and uses of mouthrinses are daily or twice daily functions for those who conscientiously care for their teeth. In fact, it is only from such continued regular use that the desirable tooth hardening effects of the fluoride-containing products will usually be obtained (unless special professional application of the tooth hardening compositions is made).

The following examples illustrate the invention but do not limit it. Unless otherwise mentioned all parts and percentages in this specification, these examples and the appended claims are by weight and all temperatures are in °C. Also, when molecular weights of the SAPP are given in the specification and claims such are determined by the vapor pressure osmometry method, as employed by the manufacturer, unless the gel permeation chromatography method (against a polyethylene glycol standard) is specified.

| Component | (toothpaste) Weight Percent |
|---|---|
| Azacycloheptane-2,2-diphosphonic acid (AHP) | 1.0 |
| Sorbitol solution, 70% active, aqueous (22.5 wt. %) | 32.1 |
| Glycerol | 11.0 |
| Carrageenan gum | 0.5 |
| Sodium fluoride | 0.24 |
| (1) Gantrez S-97, pharmaceutical grade (SAPP) | 0.5 |
| Sodium lauryl sulfate | 1.2 |
| (2) Zeodent 113 | 17.0 |
| (3) Syloid 244 | 3.0 |
| Fumed silica, thickening agent | 0.3 |
| Saccharin | 0.06 |
| Flavor (containing terpenes and mints) | 1.0 |
| Water, deionized | 32.1 |
| | 100.0 |

(1) Linear copolymer of maleic anhydride and vinyl methyl ether, of molecular weight of about 1,090,000 (by gel permeation chromatography vs. polyethylene glycol), mfd. by GAF Corp.
(2) Silica dental polishing agent, mfd. by J. M. Huber Corp.
(3) Silica thickening agent A toothpaste of the above formula is made in the manner described earlier in this specification, essentially following normal toothpaste manufacturing procedures, and is tested in vivo for its anticalculus action in comparisons with a control toothpaste that omits both the AHP and the Gantrez S-97, which are replaced with equal percentages of deionized water, and with a comparative toothpaste that omits only the Gantrez S-97. The test method is that described previously in this specification, which is published in the Gaffar et al. article appearing in Volume 26 of *Colloids and Surfaces* (1987) at pages 109-121, with twelve test animals (primates) being employed. The teeth of four of the animals were brushed with the experimental formula, the teeth of four other animals were brushed with the control formula and the teeth of the remaining four animals were brushed with the comparative formula. Brushings were once a day for one minute each time, and were continued for six weeks, after which time calculus readings were taken. Such readings are directly proportional to the extent of calculus development on the tooth surfaces of the animals tested. By such tests the control or placebo toothpaste gave a calculus reading of 8.7, the comparative gave 5.7 and the experimental gave 3.8. Thus, use of the toothpaste containing AHP alone (no SAPP) resulted in a lowering of the calculus reading by 35% but by a further addition of 0.5% of SAPP in the experimental formula an additional 33% improvement over the comparative AHP formula was obtained, based on the 5.7 and 3.8 readings, or by 63% based on the 3.0 reduction by the comparative and the additional 1.9 reduction by the experimental, and such improvement occurred despite the fact that the SAPP has negligible anticalculus action when AHP is omitted from the formula.

The described experimental toothpaste formula also acts to harden teeth, due to its content of a fluoride source (sodium fluoride), and is an effective tooth cleaner and polisher, due to its contents of surfactant and silica polishing agent. When 0.3% of triclosan is incorporated in the formula (being added to an aqueous premix solution of surfactant in water) the toothpaste acquires a significant antiplaque property, too. When the fluoride is omitted from the formula its tooth hardening action is lost but the anticalculus effect of the combination of AHP and SAPP is still obtained.

In the given formula the Zeodent 113 may be replaced by other Zeodent type polishing agents and/or by other polishing agents such as dicalcium phosphate, calcium carbonate, insoluble sodium metaphosphate and tricalcium phosphate, but the finely divided silica polishing agents are preferred and are less likely to interfere to any extent with the anticalculus action of the AHP. The sodium lauryl sulfate detergent may be replaced by other orally acceptable detergents, such as other alkali metal alkyl sulfates of 8 to 20 carbon atoms, preferably of 10 to 18 and more preferably of 2 to 16 carbon atoms in the alkyls thereof. Alternatively, other anionic, nonionic and amphoteric detergents may be employed in place of the sodium lauryl sulfate, e.g., sodium cocomonoglyceride sulfate, sodium linear tridecylbenzene sulfonate, potassium N-lauroy sarcosine, N-lauroyl, N-methyl taurate, the myristic acid ester of 1,2-dihydroxypropane sulfonate, the condensation product of a $C_{12-15}$ linear alcohol and 7 moles of ethylene oxide, the condensation product of a $C_{14-15}$ linear alcohol and about 11 moles of ethylene oxide, Pluronic F-68, Pluronic L-44, lauryl ammonium sulfonic acid betaine and Standapol ® AB-45, either separately or in mixtures. The thickener system may be replaced by other thickeners, such as carob bean gum, hydroxymethyl cellulose, Laponites ® and alginates. In place of part of the glycerol/sorbitol humectant system there may be substituted propylene glycol, polypropylene glycol and/or mannitol, and the fluoride employed may be sodium monoflurophosphate, stannous fluoride, sodium fluorosilicate or calcium fluoride. Instead of saccharin, as the artificial sweetener, aspartame may be used and the flavor may be based principally or partially on limonene and m contain menthol or other physiologically cooling agent to give it a special appeal.

It will normally be desirable for the polishing agent and any other insoluble materials present in the formula to be of part sizes no greater than 5 microns in effective diameter and preferably they will be no larger than of a mean particle size of 2 microns, as to avoid any scratching of tooth enamel during brushing of the teeth. When the composition is not to be applied with pressure against the teeth larger sized component particles may be tolerated. However, for another variation of the invented compositions, tablets which may include known tabletting compounds, such as clays and magnesium stearate, it will normally be desirable to limit the insoluble components to the sizes previously given.

When gel dentifrices are to be produced the formula of this example will be varied accordingly to produce the desired gel form, which may desirably be transparent or translucent, due to employment of a polishing agent of the Syloid ® similar type, which is of about the same refractive index as that of the gelling agent/water medium. Such polishing agents are colloidal silicas.

The various modified formulas described herein are also effective anticalculus toothpastes, gel dentifrices, etc. when the same AHP and SAPP are employed, and are also effective when other AAP's and SAPP's within the description of this specification are substituted. Similarly, such compositions and the composition of the formula given are useful in inhibiting development of calculus in humans who brush their teeth with such a composition. For best results such toothbrushings should be twice a day for at least one minute each, preferably two minutes, and brushing should continue for at least a month, preferably longer, and more preferably always. Other adjuvants may be included in the various formulas described, such as water soluble alkali metal polyphosphates, e.g., sodium pyrophosphate, to give the compositions additional desirable properties, such as tartar inhibiting action, etc. Unlike sodium pyrophosphate, which can be adversely affected by mouth enzymes, and may be protected by fluoride and SAPP against enzymatic inactivation, the AAP is stable in the presence of such enzymes and requires no stabilizer. However, if pyrophosphate is present in the formula to promote antitartar action the SAPP present with the AAP will perform the dual functions of increasing anticalculus action and stabilizing the pyrophosphate against enzymatic action (and the fluoride source will also exert such a stabilizing effect, if present).

EXAMPLE 2

| Component | (Mouthrinse) Weight Percent |
|---|---|
| Azacycloheptane-2,2-diphosphonic acid (AHP) | 0.5 |
| Gantrez S-97, pharmaceutical grade (SAPP) | 0.25 |
| Glycerol | 1.0 |
| Sodium fluoride | 0.05 |
| (4) Nonionic detergent | 1.0 |
| Flavor | 1.0 |
| Sodium saccharin | 0.03 |
| Water | 96.17 |
| | 100.0 |

(4) Pluronic F-108 or F-127, mfd. by BASF Wyandotte, Inc.

A mouthrinse of the above formula is made by mixing together the various components thereof to make a finished product suitable for use in freshening the breath and in making the teeth less liable to develop calculus deposits thereon after such repeated uses, preferably for a month or more, with application twice daily In variations of the formula when Luviform FA 139 (BASF) is substituted for the Gantrez S-97 an effective anticalculus product is obtained. Also, there is desirably substituted for 15% of the water an equal weight of ethanol (95%), which helps to solubilize the components better and has a desirable solvent action on organic materials in the saliva and on the teeth. Additionally, to aid in cleaning the oral cavity and the tooth surfaces there may desirably be present in the mouthrinse about 0.2–0.5% of surfactant (sodium lauryl sulfate is preferred), and about 0.03–0.3% of triclosan, for its antiplaque action.

To determine the extent of the improvement of anticalculus action of the AHP due to the presence of SAPP, in vitro tests were run according to the method described in the test entitled *Recent Advances in the Study of Dental Calculus* (published by IRL Press) at pages 155-173. In such test the time required for the formation of hydroxyapatite (an important element of dental calculus) on smooth hard surfaces, from a supersaturated solution of calcium phosphate, is measured, and such time is about inversely proportional to the values of anticalculus additives in such solution as anticalculus agents. To allow for dilutions of oral compositions in saliva during use and to accentuate any differences dilute solutions of additives were employed in the calcium phosphate solutions. In a control experiment, run to establish a baseline, no additives were present (only water was used to make the supersaturated solution) and it was found that hydroxyapatite formed after 17 minutes. When 0.0025% of Gantrez S-97, pharmaceutical grade was present too, hydroxyapatite formation began after 18 minutes, so the "improvement or delay in such formation was an insignificant one minute. When 0.0003% of azacycloheptane-2,2-diphosphonic acid was present, without any Gantrez S-97, hydroxyapatite formed after 30 with 0.0005% of the AHP present, without any SAPP such first formation time was 41 minutes, both of which extended times indicated significant improvements in inhibiting calculus formation. The presence of 0.0025% of the SAPP with the 0.0003% of the AHP extends the formation time to 41 minutes, which is an increase of 10 minute over the sum of the extensions due to 0.0003% of the AHP (13 minutes) and the SAPP (1 minute) over the control supersaturated aqueous calcium phosphate solution (17 minutes). Thus, such improvement, on a time basis is over 70%. The improvement obtained when 0.0005% of the AHP is present with 0.0025% of the SAPP is even greater because it takes 82 minutes then to form and deposit the hydroxyapatite. This represents an increase of 40 minutes over the expect increase of 25 minutes or an improvement of 160%. From the results of these tests it is clear that the presences of both AAP and SAPP in applicants' oral compositions result in significant improvements in such compositions' anticalculus activities.

The results of these experiments are summarized in Table 1, which follows.

TABLE 1

| Formula Components | Experiment No's., and Percentages of Components | | | | | |
|---|---|---|---|---|---|---|
| | 2A | 2B | 2C | 2D | 2E | 2F |
| Supersaturated aqueous calcium phosphate solution | 100 | 99.9975 | 99.9997 | 99.9995 | 99.9972 | 99.9970 |
| Gantrez S-97 (100% active basis) | 0 | 0.0025 | 0 | 0 | 0.0025 | 0.0025 |
| AHP | 0 | 0 | 0.0003 | 0.0005 | 0.0003 | 0.0005 |
| Hydroxyapatite formation times (minutes) | 17 | 18 | 30 | 41 | 41 | 82 |
| Unexpected delay in hydroxyapatite formation (%) | — | — | — | — | 71 | 160 |

| (Chewing Gum) | |
|---|---|
| Component | Weight Percent |
| Azacycloheptane-2,2-diphosphonic acid (AHP) | 0.2 |
| Gantrez S-97, pharmaceutical grade (SAPP) | 0.25 |
| Sorbitol/mannitol mixture (50:50) | 35.0 |
| Flavor, including 0.03% saccharin | 2.0 |
| Chicle base | 20.0 |
| Binder (starch) | 10.0 |
| Filler (talc) | 32.55 |
| | 100.0 |

Such a chewing gum is effective in inhibiting calculus deposition on teeth if chewed daily, preferably several times daily. It is also effective when the proportion of the AHP and SAPP are changed ±10, 20 and 30%, while still remaining within the ranges previously given in this specification. For best anticalculus effects the gum should be chewed one or more times daily for one or more minutes at a time for at least a month.

EXAMPLE 4

| (Lozenge) | |
|---|---|
| Component | Weight Percent |
| Azacycloheptane-2,2-diphosphonic acid (AHP) | 0.20 |
| Gantrez AN 119 (SAPP) | 0.25 |
| Sorbitol | 98.00 |
| Sodium saccharin | 0.15 |
| Magnesium stearate (tabletting agent) | 0.40 |
| Emulsifier (polysorbate 20) | 1.00 |
| | 100.0 |

A lozenge of the above formula is made by melting the sorbitol and dissolving/dispersing the other components in it, after which the mix is allowed to solidify at room temperature. The lozenges so made are effective in combatting calculus formation on teeth when used at least once a day for a month but preferably they are used twice daily for two or more months or longer and the anticalculus results will be even better.

Instead of employing sorbitol as the base other such sugars and sugar alcohols may be substituted, e.g., mannitol, sucrose and glucose, or mixtures thereof, and similar results will be obtained Alternatively, gums and gelatins may be the bases for the lozenges or candies, and the proportions of the active components may be increased, to as much as 1% of each of the AAP and the SAPP. Triclosan may be present too, with the range of contents thereof being from 0.1 to 0.6%.

EXAMPLE 5

| (Tooth Powder) | |
|---|---|
| Component | Weight Percent |
| Azacycloheptane-2,2-diphosphonic acid (AHP) | 1.0 |
| Gantrez S-97, pharmaceutical grade (SAPP) | 1.0 |
| Sodium lauryl sulfate | 0.5 |
| Zeodent 113 | 97.5 |
| | 100.0 |

The tooth powder of the above formula is made by mixing together the formula components in a suitable powder mixer. In a preferred formula there is also present about 0.2-0.8% of a suitable flavor, preferably of the mint type, e.g., peppermint, spearmint, and in an antiplaque formula triclosan is also present at a concentration of 0.1 to 0.6%, e.g., 0.3%.

The tooth powder made is good for cleaning the teeth and for protecting them against development of calculus, with resulting gum irritation that such can cause. When the triclosan is also present the powder also protects against bacterial growth that can cause the appearance of unsightly and harmful plaque. Use of the tooth powder should be regular, at least twice daily for at least a month and preferably for longer The described products, the formulas of which have been given above, may be modified by replacement of active and supplementary components with others that were previously named and referred to herein and the proportions thereof may be changed, so long as they retain within the ranges recited herein, and effective anticalculus compositions will result. While the various products, being of substantially different types, may have different properties (and may be of different physical states) normally they will be of pH's in the range of 6 to 11, preferably 7 to 9 or 10, e.g., about 7 or 8 at a 1% solution or dispersion in water at 25° C. Various other compositions for application to the teeth may be made in similar ways, such as tooth hardening agents, gel dentifrices and antiplaque compositions, with the tooth hardeners including a source of fluoride, such as 0.5% of sodium fluoride, and the antiplaque compositions containing tricloson, e.g., 0.3% thereof in the gel dentifrices and 0.03% in mouthwashes and antiplaque treatments. Also in all the working examples when the AHP is replaced by azacyclohexane-2,2-diphosphonic acid or by an AHP of the formula given wherein n is 3 and R is ethyl, or by a sodium salt thereof and when the SAPP is any of the Gantrezes described herein improved anticalculus activity is obtainable.

The invention has been described herein with references to working examples and specific embodiments thereof but is not to be limited to these because one of skill in the art with the present specification before her or him will be able to utilize substitutes and equivalents without departing from the invention.

We claim:

1. An anticalculus oral composition which comprise an orally acceptable vehicle or base for such composition, an effective anticalculus proportion of at least about 0.01% to about 5% by weight of an orally acceptable azacycloalkane-2,2-diphosphonic compound (AAP) selected from the group consisting of compounds of the formula:

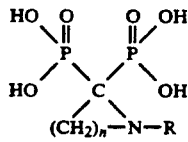

wherein R is selected from the group consisting of hydrogen and alkyls of 1 to 3 carbon atoms and n is an integer from 3 to 5, and orally acceptable salts thereof and a synthetic anionic polymeric polycarboxylate (SAPP) of a molecular weight in the range of about 5,000–2,000,000, in a proportion of at least about 0.1% to about 5% by weight, which is effective to increase the anticalculus action of the AAP in said composition.

2. An anticalculus oral composition according to claim 1 wherein the composition is a toothpaste, gel dentifrice, tooth powder, mouthrinse, mouthwash, tooth hardener, antiplaque composition, gum or lozenge, and the relative proportion of AAP to SAPP is in the range of 1:50–50:1.

3. An anticalculus oral composition according to claim 2 wherein the AAP is azacycloheptane-2,2-diphosphonic acid or a water soluble salt thereof (AHP), the SAPP is a copolymer of maleic anhydride or maleic acid with a polymerizable ethylenically unsaturated monomer or a salt of such copolymer, and the relative proportion of AHP to SAPP is in the range of about 1:10–3:1.

4. An anticalculus oral composition according to claim 3 which is a toothpaste, gel dentifrice, tooth powder, mouthrinse or mouthwash wherein the AHP is azacycloheptane-2,2-diphosphonic acid and the SAPP is a water soluble salt of a linear copolymer of maleic anhydride or maleic acid with vinyl methyl ether, which is of a molecular weight in the range of about 30,000–1,000,000.

5. An anticalculus oral composition according to claim 4 which is a toothpaste, gel dentifrice or tooth powder which comprises about 0.2–2% of AHP and about 0.2–3% of SAPP.

6. An anticalculus toothpaste or gel dentifrice according to claim 5 which comprises about 0.5–1.5% of AHP and about 0.3–1% of SAPP.

7. An anticalculus toothpaste or gel dentifrice according to claim 6 which comprises about 0.5–1.5% of azacycloheptane-2,2-diphosphonic acid, about 0.3–1% of water soluble alkali metal salt of a linear copolymer of maleic anhydride or maleic acid with vinyl methyl ether, of a molecular weight in the range of about 50,000–1,100,000, about 0.02–1% of sodium fluoride, about 10–25% of finely divided silica dental polishing agent, about 20 to 35% of glycerol and or sorbitol humectant(s), about 0.5–8% of gum and/or silica thickener(s), about 0.5–2% of a surfactant and about 35–55% of water.

8. An anticalculus toothpaste according to claim 7 which comprises about 0.1 to 0.6% of triclosan and is antiplaque.

9. An anticalculus toothpaste according to claim 7 which comprises about 0.8 to 1.2% of azacycloheptane-2,2-di-phosphonic acid, about 0.3 to 0.7% of a sodium salt of a linear copolymer of maleic anhydride or maleic acid and vinyl methyl ether, of a molecular weight in the range of 50,000 to 100,000, 0.02 to 1% of sodium fluoride, 10 to 25% of finely divided silica dental polishing agent, 20 to 35% of glycerol and/or sorbitol humectant(s), 0.5 to 8% of gum and/or silica thickener(s), 0.5 to 2% of a surfactant and 35 to 55% of water.

10. An anticalculus toothpaste according to claim 9 which comprises about 0.1–0.6% of triclosan.

11. An anticalculus oral composition according to claim 4 which is a mouthrinse or mouthwash which comprises about 0.1–2% of AHP and about 0.01–3% of SAPP in an aqueous liquid medium.

12. An anticalculus mouthrinse or mouthwash according to claim 11 which comprises about 0.1–2% of azacycloheptane-2,2-diphosphonic acid, about 0.1–3% of a sodium salt of a linear copolymer of maleic anhydride or maleic acid with vinyl methyl ether, of a molecular weight in the range of about 50,000–1,100,000, about 5–20% of ethanol and about 75.0–94.8% of water.

13. An anticalculus mouthrinse or mouthwash according to claim 12 which comprises about 0.1–0.6% of tricloson.

14. A process for treating teeth to inhibit development of calculus thereon which comprises applying to the teeth a calculus inhibiting amount of a composition of claim 1.

15. A process according to claim 14 wherein the composition applied to the teeth is a toothpaste, gel dentifrice, tooth powder, mouthrinse, mouthwash, tooth hardener, antiplaque composition, gum or lozenge, the relative proportion of AAP to SAPP is in the range of about 1:50–50:1, and the composition is applied to the teeth repeatedly.

16. A process according to claim 15 wherein the composition applied to the teeth is a toothpaste or gel dentifrice which comprises about 0.8–1.2% of azacycloheptane-2,2-diphosphonic acid about 0.3–0.7% of a sodium salt of a linear copolymer of maleic anhydride or maleic acid with vinyl methyl ether, of a molecular weight in the range of about 30,000–1,500,000, about 0.02–1% of sodium fluoride, about 10–25% of finely divided silica polishing agent, about 20–35% of glycerol and/or sorbitol humectant(s), about 1–5% of gum and/or silica thickener(s), about 0.5–2% of a surfactant, which is a synthetic organic detergent, and about 35–55% of water, and the composition is applied to the teeth at least once a day for at least a month.

17. A process according to claim 14 wherein the composition applied to the teeth is a mouthrinse or mouthwash which comprise about 0.3–1.5% of azacycloheptane-2,2-diphosphonic acid, about 0.1 1% of sodium salt of a linear copolymer of maleic anhydride or male acid with vinyl methyl ether, of a molecular weight in the range or about 50,000–1,500,000, about 5–20% of ethanol and about 77.5–94% of water, and the composition is applied to the teeth at least once a day for at least a month.

18. An anticalculus oral composition according to claim 1 wherein the SAPP is a linear copolymer of maleic anhydride or maleic acid with vinyl methyl ether, which is of a molecular weight in the range of about 1,000,000–1,100,000, as determined by gel permeation chromatography against a polyethylene glycol standard.

19. An anticalculus oral composition according to claim 4 wherein the SAPP is of a molecular weight in the range of about 1,000,000–1,100,000, as determined by gel permeation chromatography against a polyethylene glycol standard.

20. An anticalculus toothpaste or gel dentifrice according to claim 5 wherein the SAPP is of a molecular weight in the range of about 1,000,000–1,100,000, as determined by gel permeation chromatography against a polyethylene glycol standard.

21. An anticalculus mouthrinse or mouthwash according to claim 11 wherein the SAPP is of a molecular weight in the range of about 1,000,000–1,100,000, as determined by gel permeation chromatography against a polyethylene glycol standard.

* * * * *